US009770357B2

(12) United States Patent
Nayfa

(10) Patent No.: US 9,770,357 B2
(45) Date of Patent: Sep. 26, 2017

(54) ANKLE BRACE

(71) Applicant: Terry M. Nayfa, Oklahoma City, OK (US)

(72) Inventor: Terry M. Nayfa, Oklahoma City, OK (US)

(*) Notice: Subject to any disclaimer, the term of this patent is extended or adjusted under 35 U.S.C. 154(b) by 0 days.

(21) Appl. No.: 14/924,025

(22) Filed: Oct. 27, 2015

(65) Prior Publication Data
US 2016/0045353 A1 Feb. 18, 2016

Related U.S. Application Data

(63) Continuation-in-part of application No. 13/674,212, filed on Nov. 12, 2012.

(60) Provisional application No. 62/069,621, filed on Oct. 28, 2014.

(51) Int. Cl.
*A61F 5/01* (2006.01)
*A43B 7/20* (2006.01)

(52) U.S. Cl.
CPC ............. *A61F 5/0127* (2013.01); *A43B 7/20* (2013.01); *A61F 5/0102* (2013.01); *A61F 5/0195* (2013.01)

(58) Field of Classification Search
CPC .. A61F 5/00; A61F 5/01; A61F 5/0102; A61F 5/0111; A61F 5/0127; A43B 7/20
USPC ............. 602/16, 23, 27; 36/24.5, 88, 89, 92, 36/118.2, 140
See application file for complete search history.

(56) References Cited

U.S. PATENT DOCUMENTS

| | | | |
|---|---|---|---|
| 4,665,904 A | 5/1987 | Lerman | |
| 5,094,232 A | 3/1992 | Harris et al. | |
| 5,836,903 A | 11/1998 | Peters | |
| 6,146,350 A | 11/2000 | Morton | |
| 6,383,156 B1* | 5/2002 | Enzerink | A61F 5/0125 602/16 |
| 6,955,654 B2 | 10/2005 | Gilmour | |
| 7,828,758 B2 | 11/2010 | Clements et al. | |
| 8,100,845 B2 | 1/2012 | Clements et al. | |
| 2003/0014001 A1 | 1/2003 | Martin | |
| 2010/0324461 A1 | 12/2010 | Darby, II | |
| 2011/0021963 A1* | 1/2011 | Graddon | A61F 5/0111 602/27 |
| 2012/0035520 A1* | 2/2012 | Ingimundarson | A61F 5/0195 602/23 |
| 2012/0059299 A1 | 3/2012 | Clements et al. | |
| 2013/0345613 A1* | 12/2013 | Peters | A61F 5/01 602/27 |

* cited by examiner

*Primary Examiner* — Keri J Nelson

(57) ABSTRACT

An ankle brace has a stirrup with a flat bottom portion and a first and second upright leg. Each of the first and second upright legs has an upper end and a lower end, the upper end having a circular opening therethrough and the lower end attached to the flat bottom portion. First and second pivot legs, each having a circular opening therethrough, are removeably and rotatably connected to the first and second upright legs respectively. First and second leg extensions are removeably connected to the first and second pivot legs, respectively. When connected, the circular openings in the pivot legs overlap the respective circular openings in the upright legs, and each pivot leg is rotatable about an axis through and perpendicular to the pivot leg circular opening. The circular openings in the first and second upright legs are positioned and sufficiently large to allow at least a portion of the malleolus bone of an ankle to protrude therethrough.

13 Claims, 15 Drawing Sheets

ANKLE BRACE

CROSS-REFERENCE TO RELATED APPLICATIONS/INCORPORATION BY REFERENCE STATEMENT

This application is a continuation-in-part of U.S. Ser. No. 13/674,212 filed Nov. 12, 2012, and also claims priority to U.S. provisional application Ser. No. 62/069,621 filed Oct. 28, 2014, the contents each of which are hereby incorporated in their entirety.

BACKGROUND OF THE INVENTIVE CONCEPTS

1. Field of the Inventive Concepts

The inventive concepts disclosed and claimed herein relate generally to orthopedic devices, and more particularly, but not by way of limitation, to an ankle brace.

2. Brief Description of Related Art

Ankle injuries are among the most common injuries in sports. When an ankle is injured, the traditional methods for promoting healing include application of pressure to the area to reduce swelling and to prevent movement of the ankle. The current trend in medicine now is to promote exercise as soon as possible after an ankle injury. It is therefore desirable to provide an orthopedic device or orthosis which allows exercise of the injured ankle while additionally resisting mobility in the direction which would irritate the injury.

An ankle orthosis is typically a brace that surrounds the ankle and provides pressure while controlling the ankle movement. The orthosis can be designed to allow forward and backward flexing while preventing lateral movement of the ankle, i.e., inward and outward flexing. This is accomplished using a brace with upper and lower portions hinged at the ankle bone position allowing the brace to pivot backwards and forwards. Unfortunately, location of a hinge or rivet adjacent the ankle bone can cause pressure, rubbing and irritation of the protruding ankle bones.

To alleviate the pressure on and irritation to the ankle bones, one prior art device utilizes a circular hinge with hinge openings sufficiently large to accommodate protrusion of the ankle bone (see U.S. Pat. No. 4,665,904). Unfortunately, this circular hinge device is not separable. Ankle braces having a separable hinge, such as the brace described in U.S. Pat. No. 6,146,350, can be less difficult to manufacture in that separate steps are not required to connect the upper and lower portions of the brace. A separable hinge design also allows a user to remove the upper portion of the brace while leaving the lower portion inserted in the shoe for storage. However, prior art ankle braces having detachable hinges are bulky and require the detachable hinge surface to rotate about the ankle bone when worn, causing irritation as described above.

In view of the foregoing, there is a need for a less bulky ankle brace having upper and lower portions that are removeably, releasably and rotatably connected about the ankle bone area, while reducing or eliminating contact of the hinge surface with the ankle bone. It is to such a comfortable and user-friendly ankle brace design that the presently disclosed and claimed inventive concept(s) is directed.

SUMMARY OF THE INVENTIVE CONCEPTS

The inventive concepts disclosed and claimed herein generally relate to an ankle brace. The ankle brace has a stirrup and first and second pivot legs. The stirrup has a flat bottom portion and a first and second upright leg. Each of the first and second upright legs has an upper end with a circular opening therethrough, and a lower end that attaches to the flat bottom portion. The first and second pivot legs each have a circular opening therethrough and are removeably, releasably, and rotatably connected to the first and second upright legs respectively. When connected, the circular openings in the pivot legs overlap the respective circular openings in the upright legs, and each pivot leg is rotatable about an axis through and perpendicular to the pivot leg circular opening. When the ankle brace is worn, the circular openings in the first and second upright legs are positioned and sufficiently large to allow at least a portion of the malleolus bone of an ankle to protrude therethrough. First and second leg extensions are connectable to the first and second pivot legs, respectively, to provide additional support.

BRIEF DESCRIPTION OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, and drawings. The figures are not necessarily the scale and certain features and certain views of the figures may be shown exaggerated, to scale or in schematic in the interest of clarity and conciseness. In the drawings.

DETAILED DESCRIPTION OF EXEMPLARY EMBODIMENTS

Figure 1:
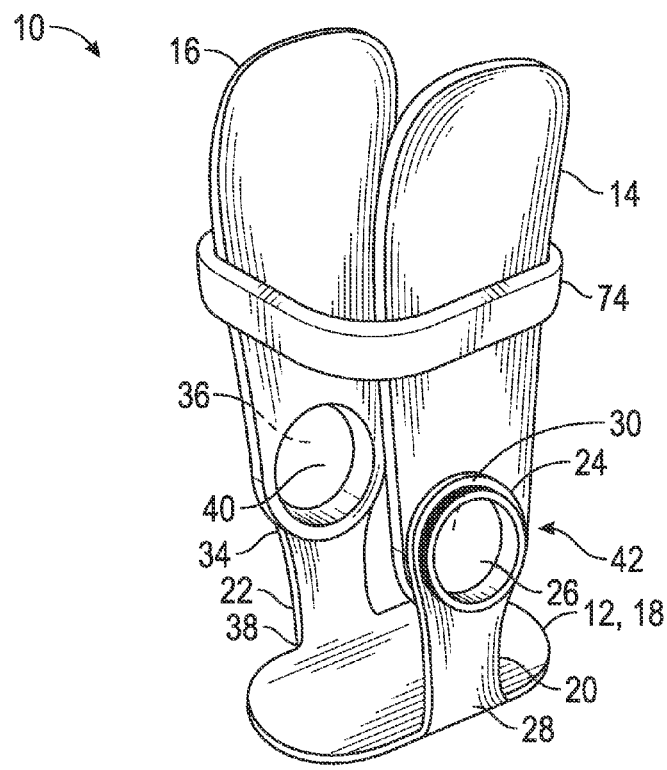
FIG. 1 is a perspective view of an ankle brace constructed in accordance with the inventive concepts disclosed herein.

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless it is obvious that it is meant otherwise.

Use of the term "malleolus" refers to either of the two rounded prominences or protuberances on either side of the ankle joint. The lateral (or fibular, external, or outer) malleolus is at the lower end of the fibula and the medial (or tibial, internal, or inner) malleolus is at the lower end of the tibia.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings, and more particularly to FIG. 1, shown therein is an exemplary embodiment of an ankle brace 10 constructed in accordance with the inventive concepts disclosed and claimed herein. The ankle brace 10 has a stirrup 12, a first pivot leg 14 and a second pivot leg 16. The stirrup 12 has a flat bottom portion 18, a first upright leg 20 and second upright leg 22. The first upright leg 20 has a first upper end 24 with a first circular opening 26 therethrough, and a first lower end 28 that attaches to the flat bottom portion 18. The first pivot leg 14 has a first circular pivot opening 30 therethrough and is releasably and rotatably connected to the first upright leg 20. When connected, the first circular pivot opening 30 overlaps the first circular opening 26 and the first pivot leg 14 is rotatable about an axis 32 through and perpendicular to the first circular pivot opening 30.

Similarly, the second upright leg 22 has a second upper end 34 with a second circular opening 36 therethrough, and a second lower end 38 that attaches to the flat bottom portion 18. The second pivot leg 16 has a second circular pivot opening 40 therethrough and is releasably and rotatably connected to the second upright leg 22. When connected, the second circular pivot opening 40 overlaps the second circular opening 36 and the second pivot leg 16 is rotatable about an axis 32' through and perpendicular to the second circular pivot opening 40. When the ankle brace 10 is worn, the first and second circular openings 26 and 36, respectively, are positioned and sufficiently large to allow at least a portion of the malleolus of an ankle to protrude therethrough. Thus the ankle brace 10 pivots along the same axis as the foot, allowing forward and backward flexing (plantar flexion and dorsiflexion) while limiting inward and outward flexing (inversion and eversion) and reducing or eliminating irritation due to contact of the hinge surface with the ankle bone.

The stirrup 12 can be a single integral piece formed to define the flat bottom portion 18 and the first and second upright legs 20 and 22, respectively. The first and second upright legs 20 and 22 extend substantially vertically from the flat bottom portion 18. The stirrup 12 conforms closely to the shape of the foot and can be worn inside a user's shoe. In one embodiment, the first and second upright legs 20 and 22 are mirror images of each other, allowing a right ankle brace to be interchangeable with a left ankle brace. In another embodiment, the first and second upright legs 20 and 22, respectively, are not mirror images and can be slightly offset to compensate for a slight pronation or supination.

The stirrup 12 and the first and second pivot legs 14 and 16, respectively, can be made of any material providing semi-rigid support and compatible the foot and ankle. In one embodiment, the stirrup 12 and the first and second pivot legs 14 and 16, respectively, are made of a semi-rigid, thin wall thermoplastic such as polyethylene, polyurethane, polypropylene, polycarbonate, and/or acrylic. In another embodiment, these components are made of polyethylene.

Figure 2:
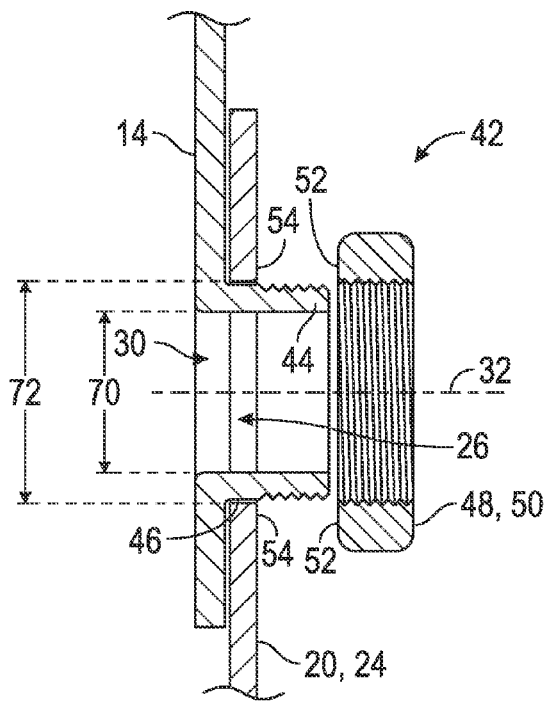
FIG. 2 is a sectional view of a hinge assembly of the ankle brace.

In one embodiment, the first pivot leg 14 is releasably and rotatably connected to the first upright leg 20 using a hinge assembly 42. Because the second pivot leg 16 can be releasably and rotatably connected to the second upright leg 22 using an identical hinge assembly, only one hinge assembly 42 will be described. Referring now to FIG. 2, the first pivot leg 14 can include a round neck 44 about the first circular pivot opening 30. The neck 44 can be an integral part of the first pivot leg 14 and provides a pivot surface 46 on which the first upright leg 20 and the first pivot leg 14 can rotate about the axis 32. The first upright leg 20 is rotatably secured to the first pivot leg 14 using a retaining member 48. A user can remove the retaining member 48 from the neck 44 to disconnect the first upright leg 20 from the first pivot leg 14.

In the embodiment shown in FIG. 2, the retaining member 48 is internally threaded and sized to receive an externally threaded neck 44. The retaining member 48 can be configured as a collar 50 with a retaining surface 52 positionable adjacent a perimeter 54 of the first circular opening 26. A user can readily secure or remove the first pivot leg 14 by attaching or removing the collar 50.

Figure 3:
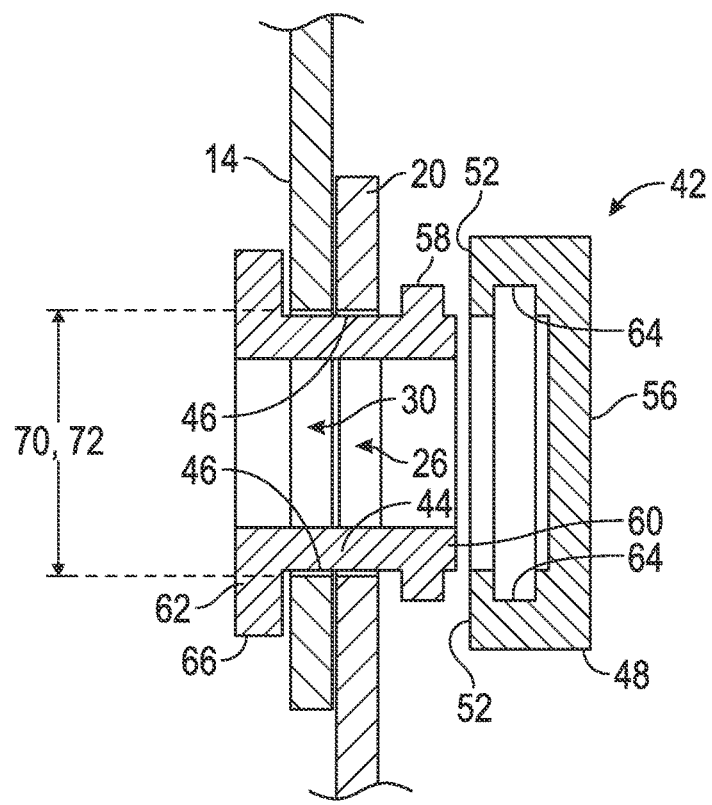
FIG. 3 is a sectional view of a hinge assembly for another embodiment of the ankle brace.

While the retaining member 48 is shown in FIG. 2 as an open collar 50 threadingly securing the first pivot leg 14 to the first upright leg 20, other shapes and mechanisms of attachment can be used. For example, the retaining member 48 can include an end cap 56 and can utilize a snap fit attachment mechanism as shown in FIG. 3. The snap fit can be achieved, for example, by using an annular ring 58 along an outer edge 60 of the tubular neck 44 on a grommet 62 such that compression of the retaining member 48 against the grommet 62 causes the annular ring 58 to snap fit within an annular groove 64 on the retaining member 48. Addition of the end cap 56, while adding bulk to the overall ankle brace 10, can provide additional structural integrity to the retaining member 48 while still maintaining an open space for the malleolus.

The tubular neck 44 of the grommet 62 can be sized to fit through the first circular pivot opening 30 and the first circular opening 26, while a flange 66 of the grommet 62 is sized larger than the openings 30 and 26, respectively, to act as a stop. To attach the first pivot leg 14 to the first upright leg 20, the outer edge 60 of the grommet 62 can be inserted through the first circular pivot opening 30 in the first pivot leg 14 and through the first circular opening 26 in the first upright leg 20. The retaining member 48 can then be snapped onto the outer edge 60 of the grommet 62. Thus the flange 66 retains the grommet 62 on one side of the hinge assembly 42 while the retaining member 48 retains the grommet on the opposite side of the hinge assembly 42. The pivot surface 46 allows rotation of the first pivot leg 14 with respect to the first upright leg 20. If desired, the flange 66 can be glued or otherwise made to adhere to the first pivot leg 14 causing the flange 66 to rotate with the first pivot leg 14.

Figure 4:
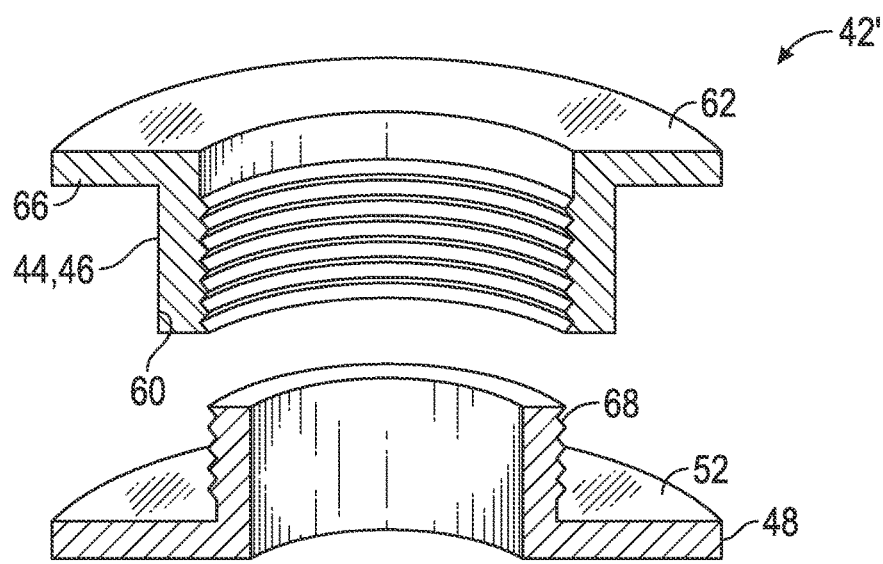
FIG. 4 is a sectional view of a removable grommet and retaining member for use in an embodiment of the ankle brace.

FIG. 4 shows another variation of a hinge assembly 42 having a removable grommet 62 and retaining member 48. The tubular neck 44 of the grommet 62 is shown as internally-threaded and sized to receive an externally threaded tubular portion 68 of the retaining member 48. The external surface of the tubular neck 44 provides the pivot surface 46 on which the first upright leg 20 and the first pivot leg 14 can rotate. Assembly and disassembly of the hinge 42' can be accomplished as described above with screw tightening of the retaining member 48 rather than with a snap fit.

The first and second circular pivot openings 30 and 40, respectively, as well as the first and second circular openings 26 and 36, respectively, are sized to accommodate protrusion of the malleolus or ankle bone. In one embodiment, the inside diameters 70 and 72 of the first circular pivot opening 30 and the first circular opening 26, respectively, are between 1¼ inches and 2½ inches. When the ankle brace 10 is designed as in FIG. 2 with the neck 44 an integral part of the first pivot leg 14, then the inside diameter 72 of the first circular opening 26 is slightly larger than the inside diameter 70 of the first circular pivot opening 30 to accommodate insertion of the neck 44 therethrough.

The ankle brace 10 can be secured and tightened to a user's lower leg and ankle using a variety of strap-type fasteners which can circumscribe at least a portion of the first and second pivot legs 14 and 16, respectively. For example, a strap 74 can attach to the first and second pivot legs 14 and 16, respectively, and to itself using methods known to those skilled in the art such as VELCRO® and other hook and loop type attachments. The strap 74 can be made of any suitable material such as nylon or a flexible and/or stretchable material such as an elastic fabric cloth. In one embodiment, the strap 74 can be tightened about the leg using standard lacing to avoid harming delicate clothing with VELCRO®-type hook material.

Padding can be placed on surfaces of the stirrup and/or pivot legs that are in contact with the user's skin or sock when wearing the ankle brace 10. The padding can be attached to these surfaces using, for example, VELCRO® strips glued, stitched or otherwise adhered to the surfaces and to the padding. Such use and attachment of padding to ankle braces is well known to those skilled in the art.

Figure 5A:
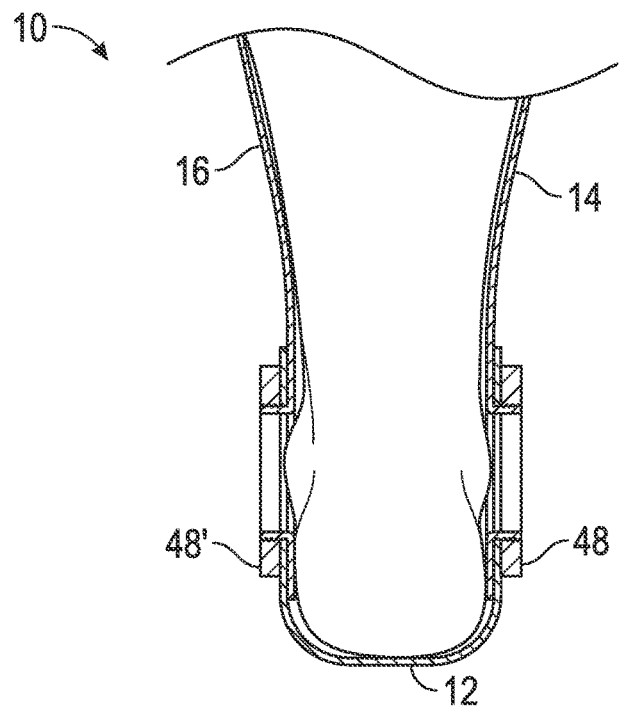
FIGS. 5A and 5B illustrate the snug fit obtained using an ankle brace constructed in accordance with the inventive concepts disclosed herein compared to the bulkiness of a prior art ankle brace.
Figure 5B:
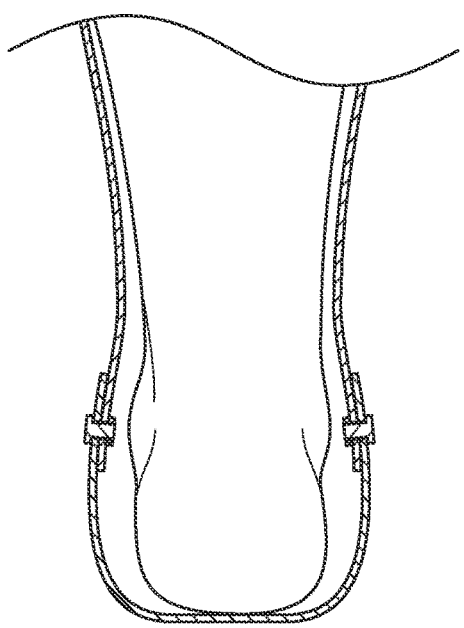

An ankle brace 10 constructed in accordance with the inventive concepts disclosed herein is viewed on the foot of a user in FIG. 5A, demonstrating how much closer the ankle brace can conform to the heel and ankle area of the foot compared to the bulkiness of a prior art ankle brace shown in FIG. 5B. This allows the user to more readily insert the stirrup 12 into a shoe. When not wearing the ankle brace 10, the user may choose to leave the stirrup 12 beneath, for example, a gel pad in a tennis shoe, and remove the first and second pivot legs 14 and 16, respectively, by detaching the retaining members 48 and 48'. This allows the shoes to be stored normally in, for example, a standard shoe box, without removal of the stirrup and padding. As the ankle mends and the entire ankle brace 10 is no longer necessary, a user may choose to wear only the stirrup 12. By wearing only the stirrup 12, a level of protection and support is still provided, but with even less bulk about the ankle and calf.

Typically, ankle braces are hinged with the pivot legs adjacent the ankle and the upper end of the upright legs external to the pivot legs as shown in FIG. 5B. This is done to reduce the rubbing and irritation of the ankle that occurs with forward and backward flexing. However, the presently disclosed ankle brace 10 reduces the contact of the brace with the ankle sufficiently to allow hinging with the first and second upright legs 20 and 22, respectively, adjacent the ankle and the first and second pivot legs 14 and 16, respectively, external to the upright legs. Such arrangement even further reduces the bulkiness of the ankle brace 10 allowing the ankle brace 10 to be even more readily fit within a shoe.

Figure 6:
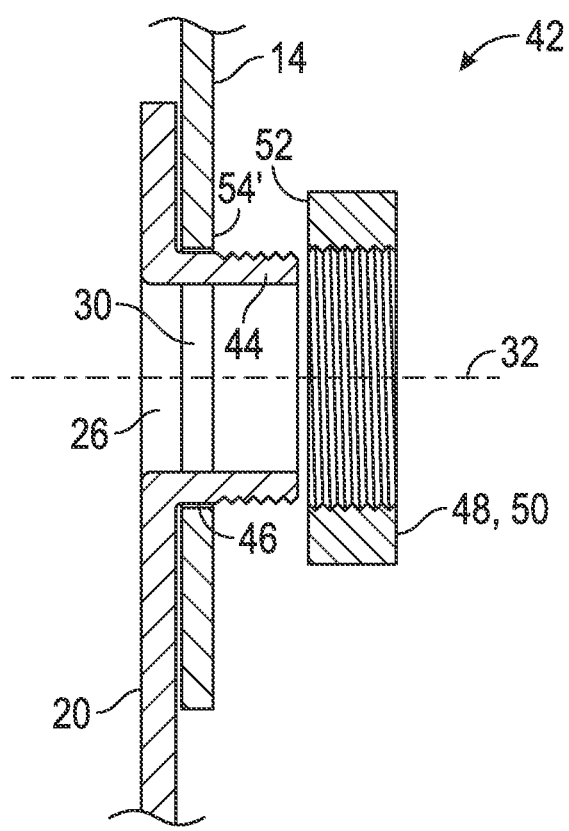
FIG. 6 is a sectional view of a hinge assembly for yet another embodiment of the ankle brace.

For example and referring now to FIG. 6, in one embodiment, the first upright leg 20 includes a round neck 44 about the first circular opening 26. The neck 44 can be an integral part of the first upright leg 20 and provides a pivot surface 46 on which the first upright leg 20 and the first pivot leg 14 can rotate about the axis 32. The first pivot leg 14 is rotatably secured to the first upright leg 20 using a retaining member 48 as described previously. The retaining member 48, when configured as a collar 50, has the retaining surface 52 positionable adjacent a perimeter 54' of the first circular pivot opening 30. As previously described, a user can remove the retaining member 48 from the neck 44 to disconnect the first upright leg 20 from the first pivot leg 14.

Prototype Examples

Figure 7:
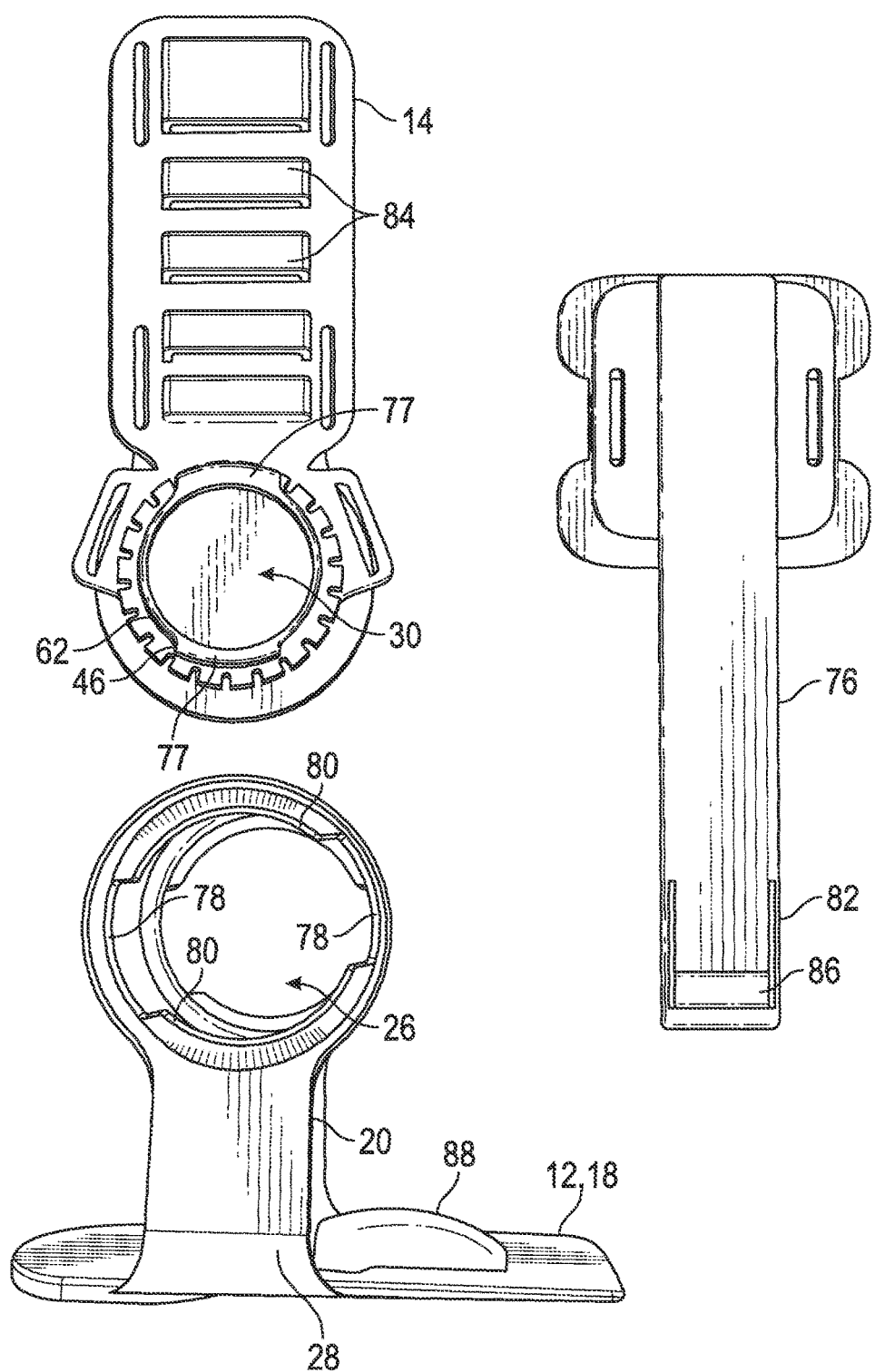
FIG. 7 is a front view of an example stirrup, pivot leg and unassembled hinge assembly.

An exemplary ankle brace 10 was manufactured as a prototype using CAD programming and 3-D printing. FIG. 7 shows the stirrup 12, first pivot leg 14, and unassembled hinge assembly 42 of this exemplary prototype, as well as a leg extension 76. The pivot leg 14 includes pivot surface 46 as in FIG. 2; however, rather than utilizing an externally threaded neck 44, the example prototype includes tabs 77 which can be fit through tab openings 78 and held in place in upright positions by a flange area 80. This allows for very simple removal and addition of the first pivot leg 14.

The example prototype includes the leg extension 76 which can be used to extend support of the calf at different heights up to the user's knee. The lower portion 82 of the leg extension 76 can be inserted through the extended slots 84 of the first pivot leg 14. A row of multiple extended slots 84 form a channel for inserting the leg extension 76. Securing member 86 catches between each set of extended slots 84, and thus can be positioned at a height desired by the user.

Figure 8:
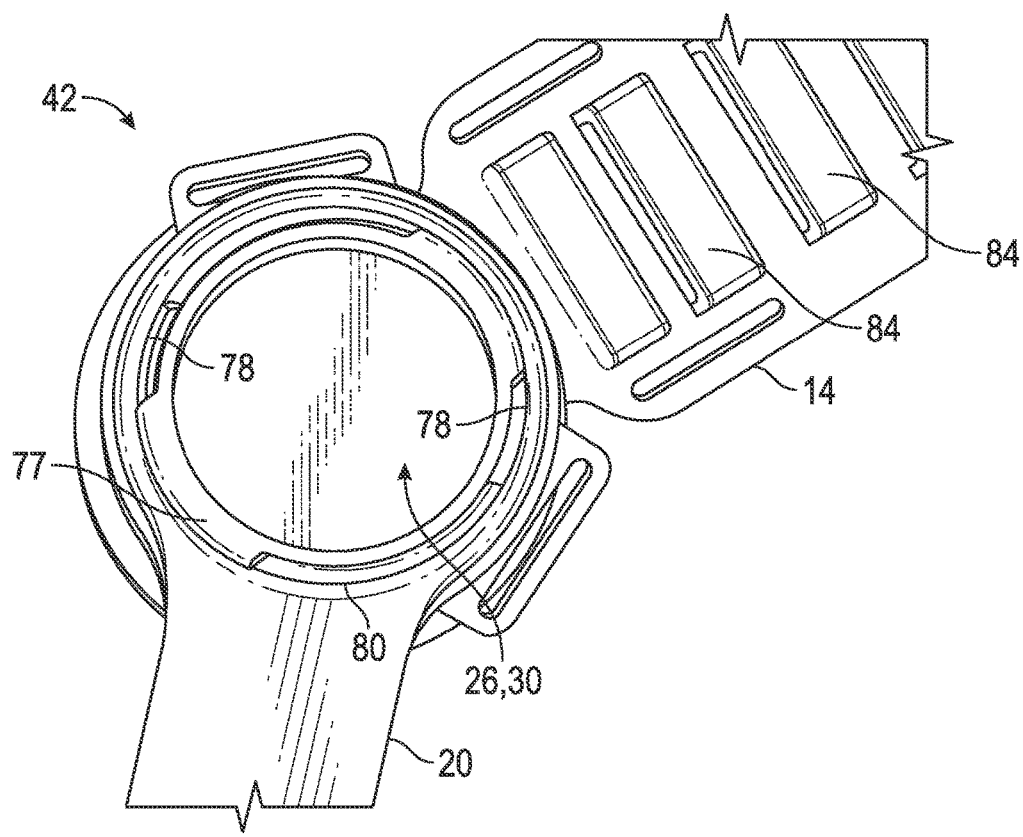
FIG. 8 is a front view of the hinge assembly in FIG. 7.
Figure 9:
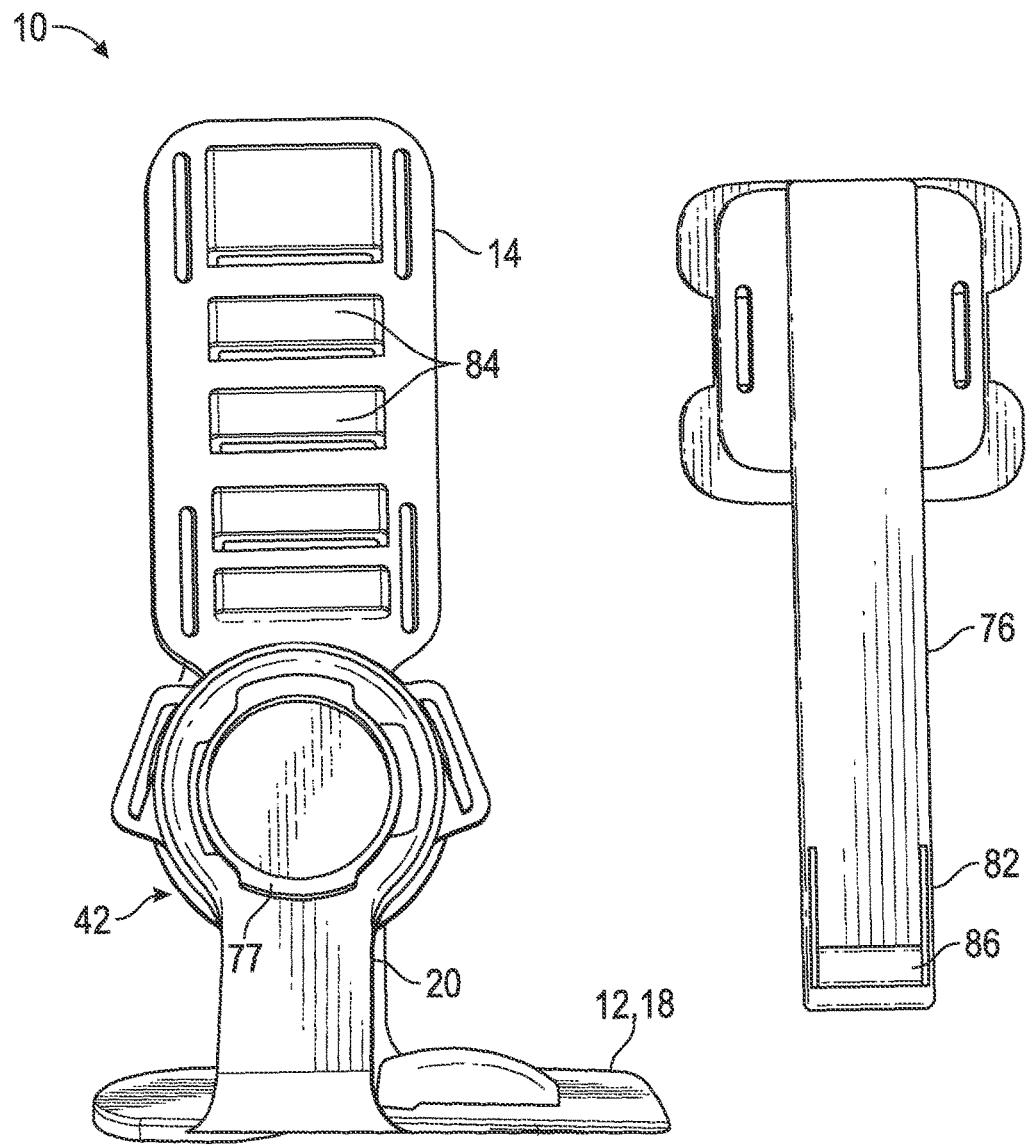
FIG. 9 is a front view of the stirrup and the first pivot leg of FIG. 7 in an assembled configuration with the leg extension not yet inserted.
Figure 10:
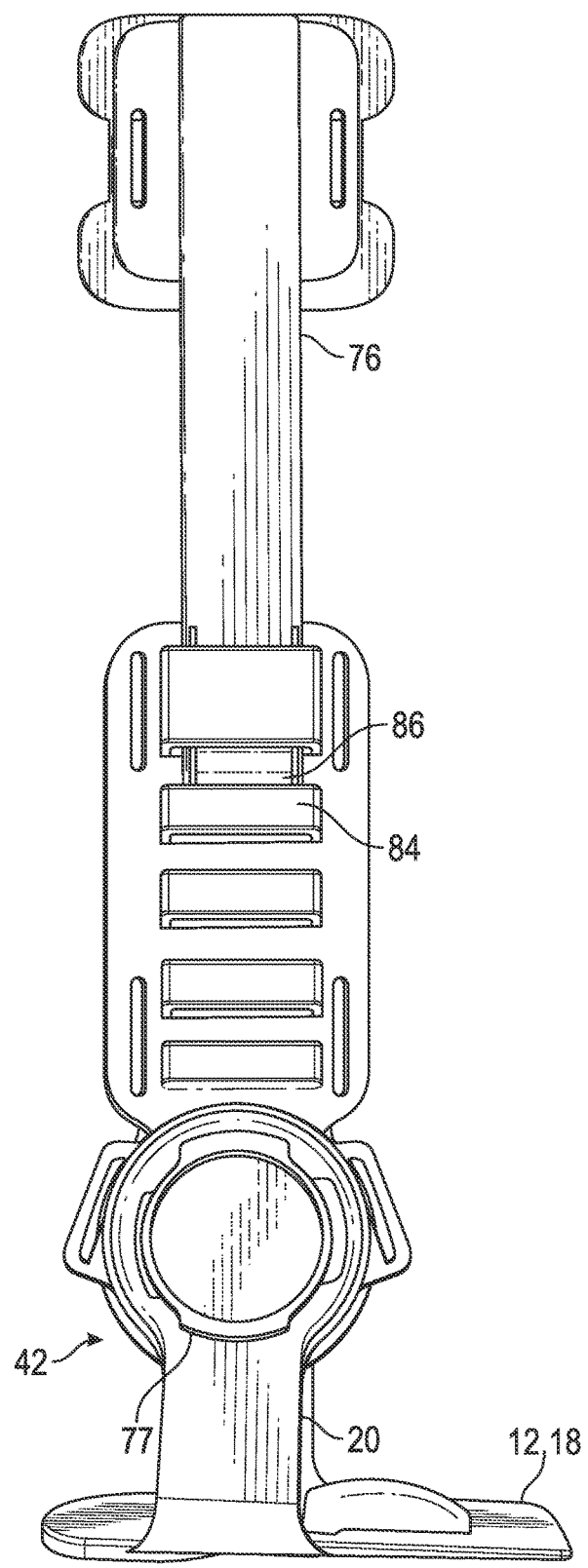
FIG. 10 is a front view of the leg extension of FIG. 7 inserted into the extended slots in an uppermost position.

FIG. 8 is a close-up view of the hinge assembly 42 of the example prototype. FIG. 9 shows the example prototype stirrup 12 and the first pivot leg 14 in an assembled configuration with the leg extension 76 not yet inserted. FIG. 10 shows the leg extension 76 inserted into the channel formed by the multiple extended slots 84 with the securing member 86 in an uppermost position.

Figure 11:
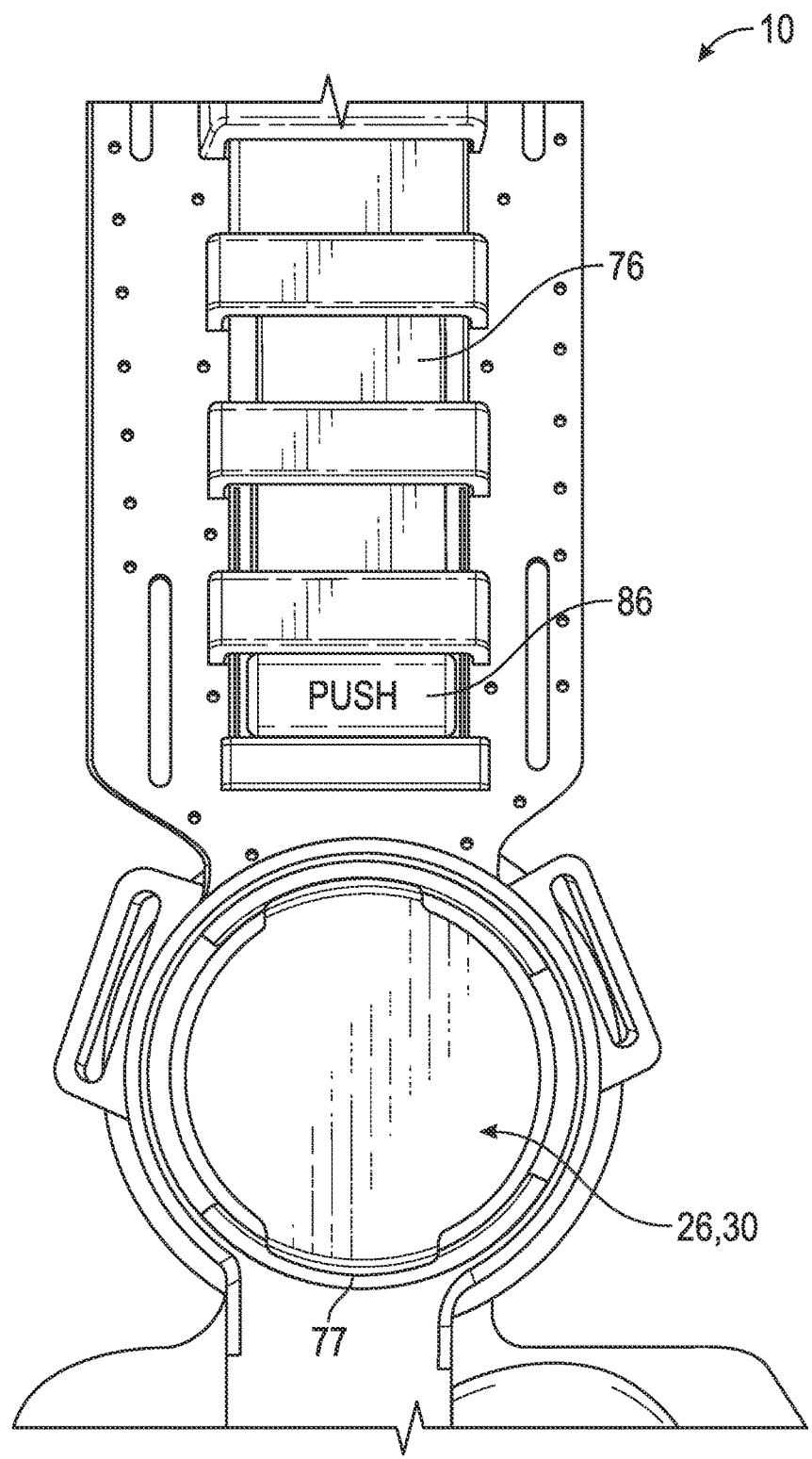
FIG. 11 is a front view of the leg extension of FIG. 7 in the lowest position.
Figure 12:
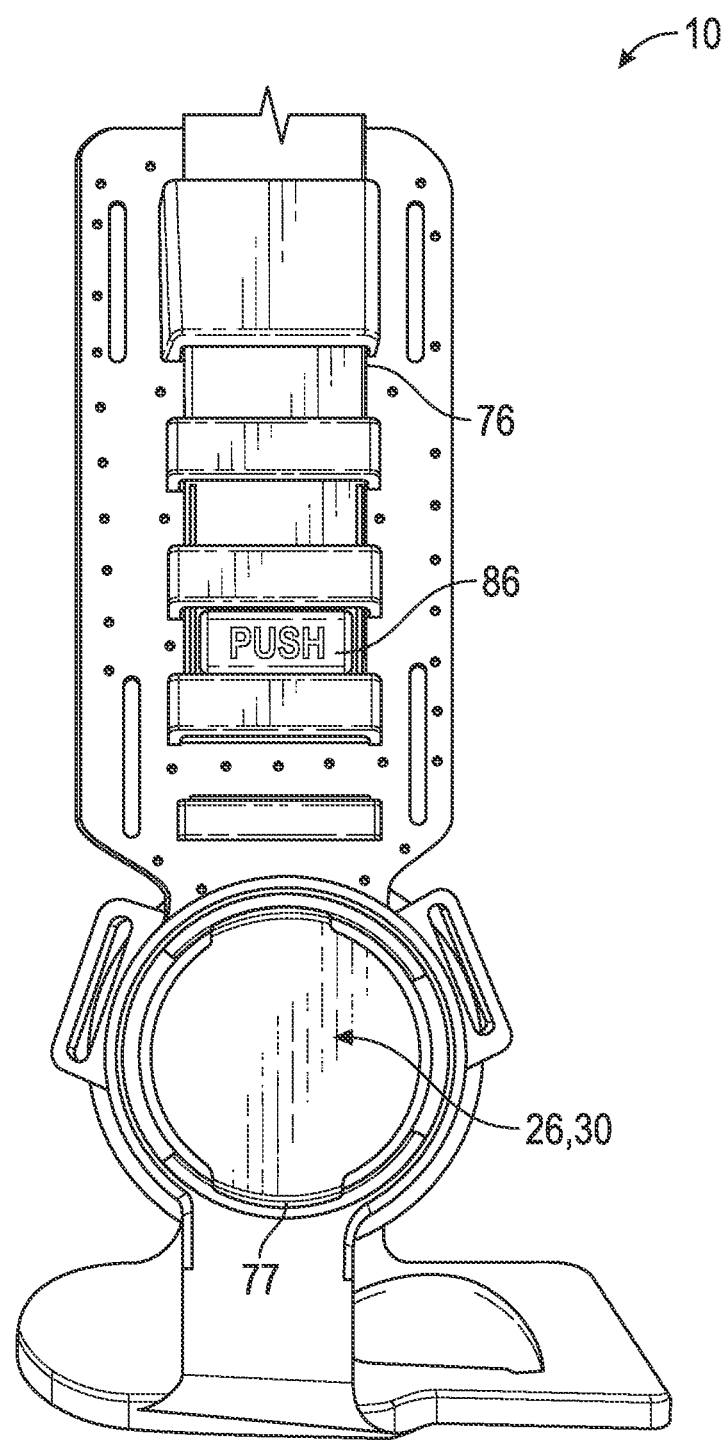
FIG. 12 is a front view of the leg extension of FIG. 7 in a second position.
Figure 13:
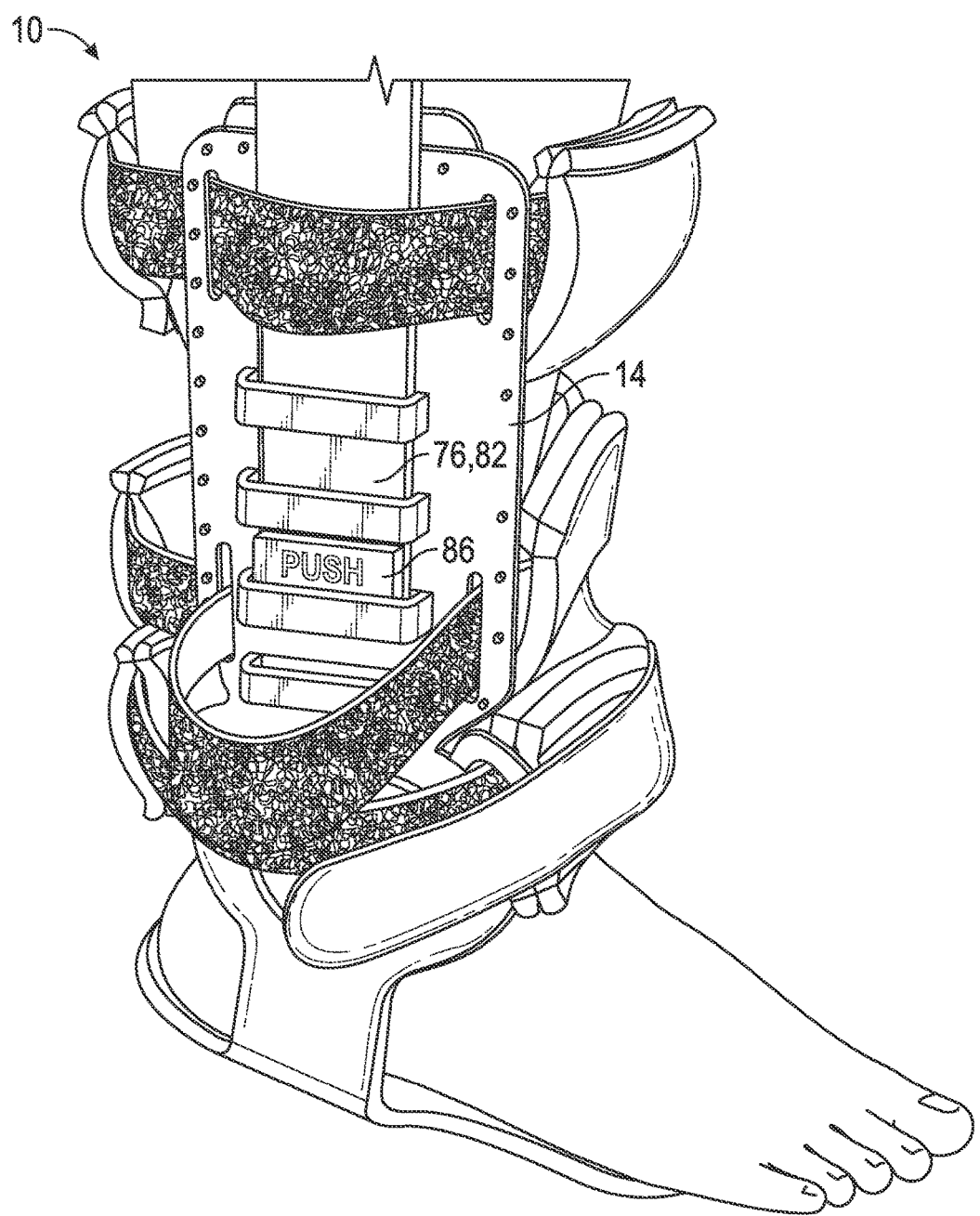
FIG. 13 shows the ankle brace worn by a person using the second position of FIG. 12.

FIG. 11 is a close-up view of the leg extension 76 in the lowest most position. By pushing the securing member 86 where indicated by the word "PUSH," the leg extension 76 can be extended to a second position as shown in FIG. 12. The view in FIG. 13 shows the ankle brace 10 being worn using this second position. VELCRO® straps are shown loose and the position of the lower portion 82 of the leg extension 76 and the securing member 86 can be seen.

Figure 14:
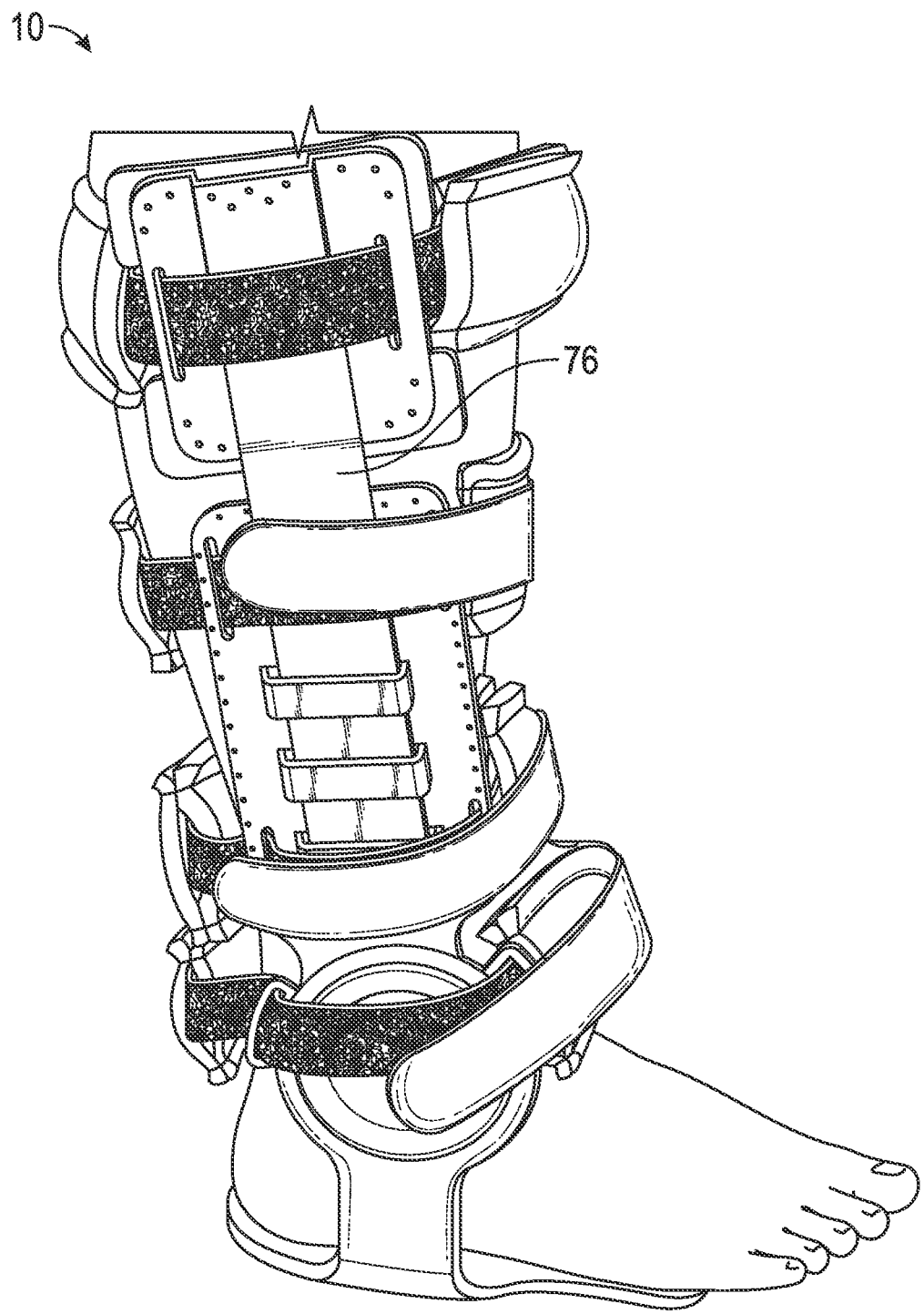
FIG. 14 shows the increased calf coverage provided by repositioning the leg extension.
Figure 15:
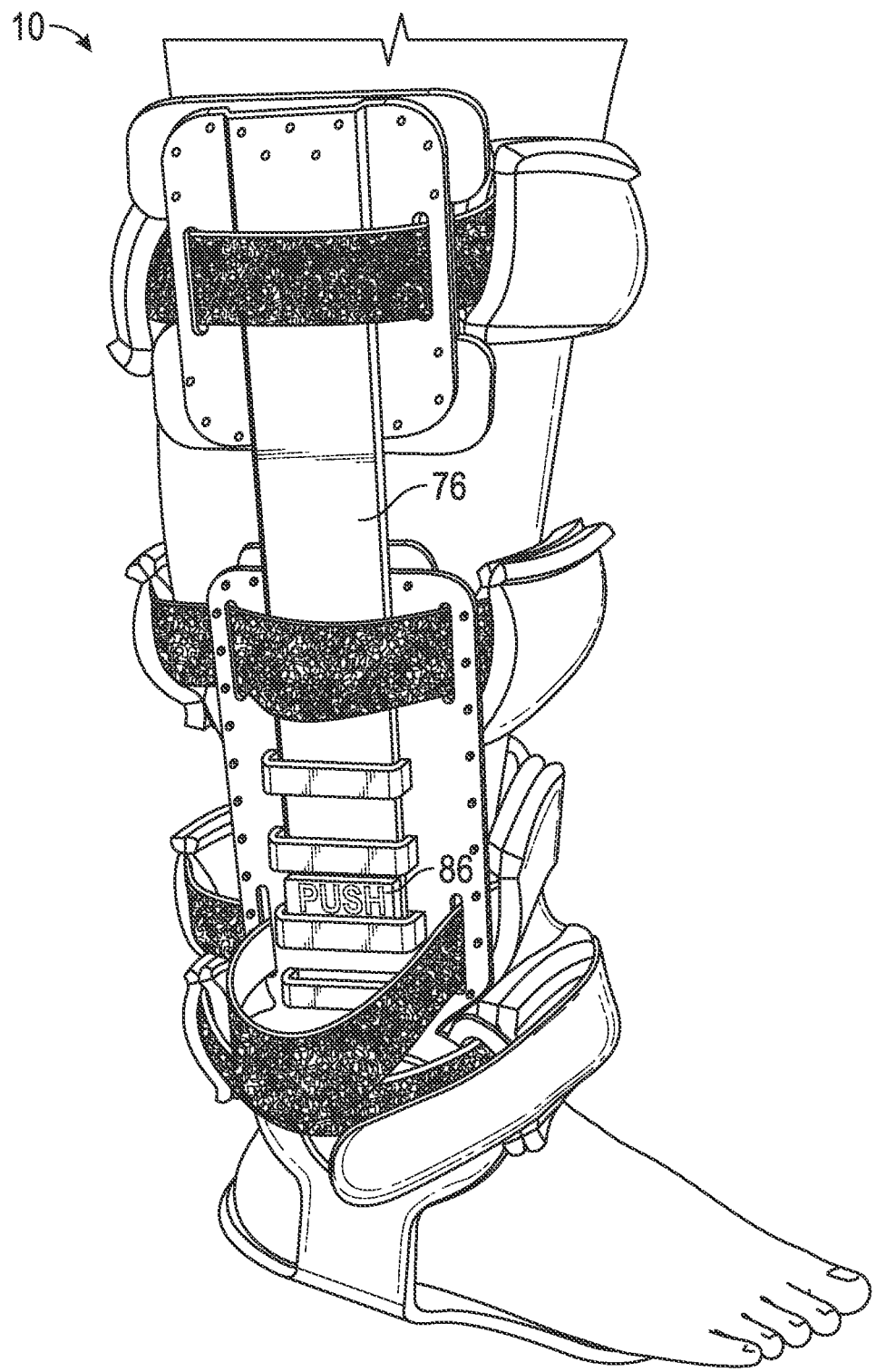
FIG. 15 and FIG. 16 show the leg extension positioned to increasingly higher positions on the leg.
Figure 16:
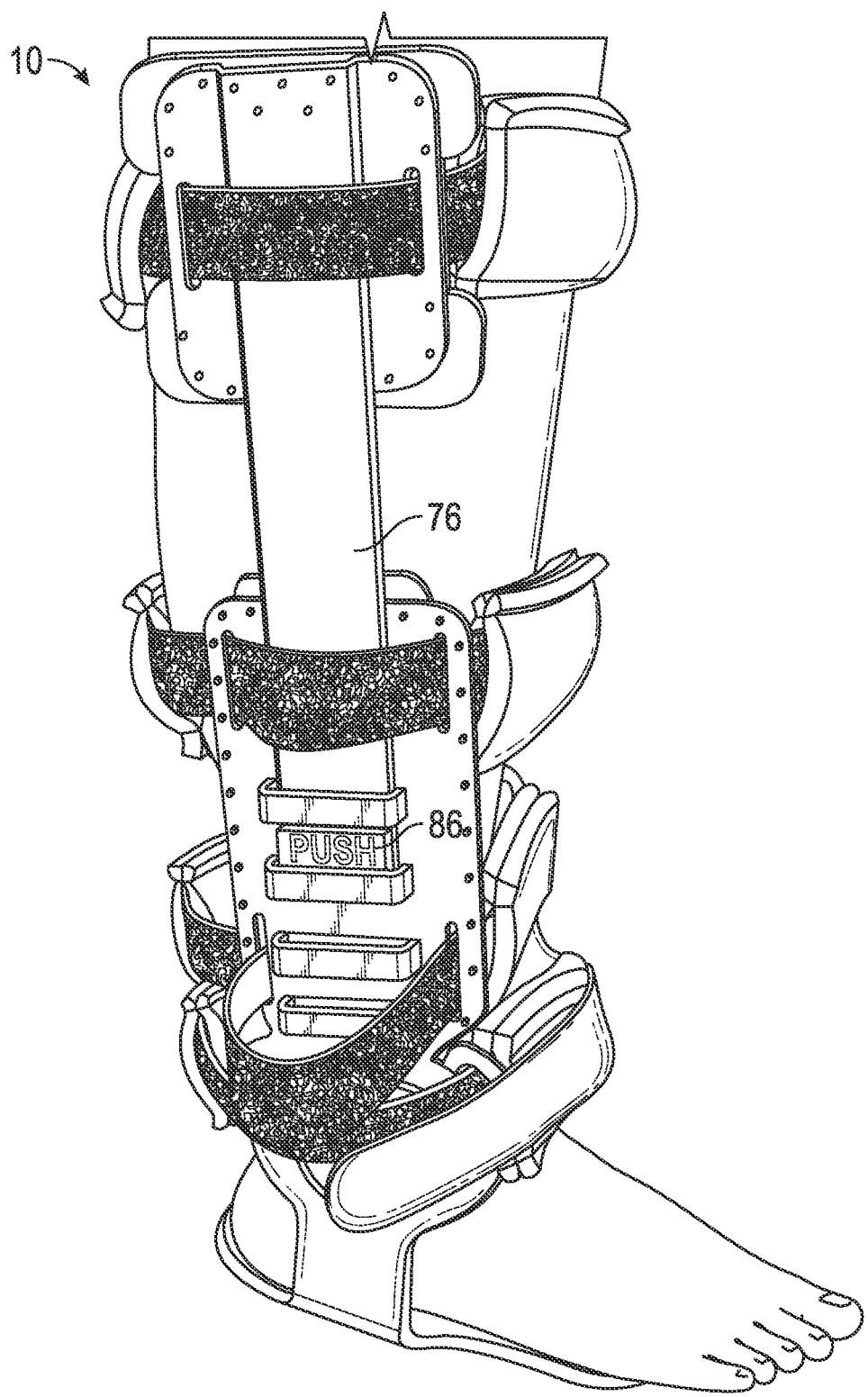

In FIG. 14 the user has moved the securing member 86 to a yet higher position and has thereby increased calf coverage of the ankle brace 10. As can also be seen, the VELCRO® straps have been tightened securing the ankle brace 10 to the user. FIG. 15 and FIG. 16 show the leg extension 76 positioned to increasingly higher positions on the user's leg.

Figure 17:
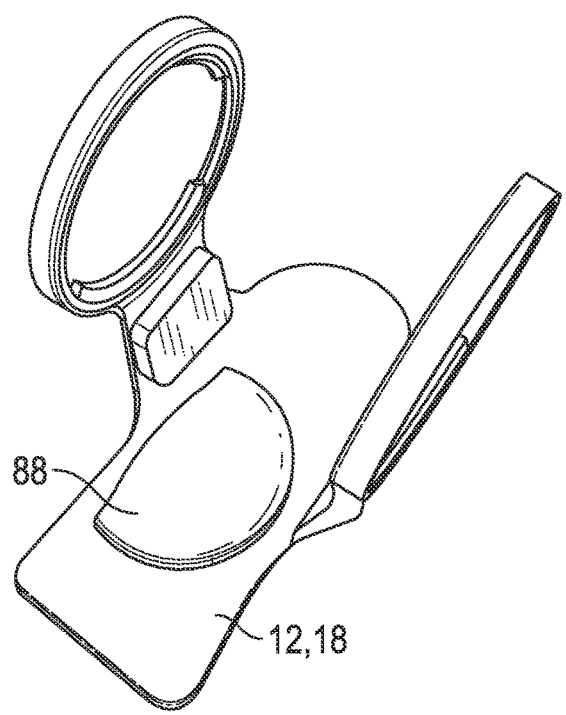
FIG. 17 is a perspective view of an example arch support added to the flat bottom portion of the ankle brace.

An arch support 88 can be added to the flat bottom portion 18 of the ankle brace 10 as shown in FIG. 17. The arch support 88 can be made of any material compatible with the user and the ankle brace 10, and can be positioned by a professional to better fit the individual user and the user's needs. The arch support 88 can be attached to the flat bottom portion 18 using adhesives and other means known by those skilled in the art.

Figure 18:
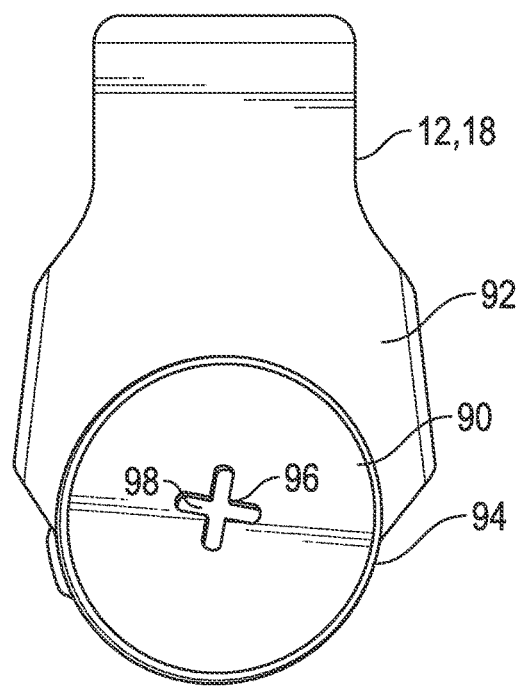
FIG. 18 is a bottom view of an example orthotic heel correction providing a tilt to the heel portion of the stirrup.

In the example prototype shown in FIG. 18, an orthotic heel correction 90 is included at the heel portion 92 of the stirrup 12. Orthotic heel corrections 90 are commonly referred to as wedges, and can be provided with a variety of angles. A podiatrist can select the appropriate wedge angle and attach the orthotic heel correction 90 to a bottom heel portion 92 of the stirrup 12. The orthotic heel correction 90 shown in FIG. 18 has a 4° tilt and fits into a circular recess 94 on the bottom heel portion 92 of the stirrup 12. It can be attached using an adhesive compatible with surrounding materials. In the example prototype shown in FIG. 18, a cutaway 96 in the orthotic heel correction 90 is matched in size and shape with an upraised portion 98 of the stirrup 12 to keep the orthotic heel correction 90 from slipping or rotating position. The upraised portion 98 shown in FIG. 18 has four arms 100. Thus the tilt can be adjusted to four positions, each 90° from one another. The upraised portion can have any number of arms. For example, using six equally spaced arms would provide six possible tilt positions, each 40° from one another.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished without departing from the scope of the inventive concepts disclosed herein and defined by the appended claims.

What is claimed is:

1. An ankle brace, comprising:
    a stirrup having a flat bottom portion and a first and second upright leg, each of the first and second upright legs having an upper end and a lower end, the upper end having a circular opening therethrough and the lower end attached to the flat bottom portion;
    first and second pivot legs rotatably connected to the first and second upright legs at first and second hinge assemblies respectively, and wherein the first and second pivot legs are releasably removable from the first and second upright legs at the first and second hinge assemblies respectively, each hinge assembly and each of the pivot legs having a circular pivot opening therethrough such that in a connected configuration, each circular pivot opening overlaps the circular opening in the respective upright leg, and each pivot leg is rotatable about an axis through and perpendicular to the circular pivot opening when the ankle brace is worn; and
    first and second leg extensions connectable to the first and second pivot legs, respectively;
    wherein the circular openings in the first and second upright legs and the circular pivot openings are positioned and sufficiently large to allow at least a portion of each malleolus of an ankle to protrude therethrough when the ankle brace is worn; and
    wherein the first hinge assembly consists of a neck about the circular pivot opening in the first pivot leg, two or more tabs at a distal end of the neck, and tab openings along the circular opening in the first upright leg, the neck and tabs extendable through the circular opening in the first upright leg when the two or more tabs are aligned with the tab openings, the first upright leg rotatable about the neck and securable to the neck by the two or more tabs in the connected configuration.

2. The ankle brace of claim 1, wherein the first and second leg extensions are extendible to provide varying amounts of extension.

3. The ankle brace of claim 2, wherein the first and second leg extensions are removably connected to the first and second pivot legs, respectively.

4. The ankle brace of claim 1, wherein the first and second leg extensions are removably connected to the first and second pivot legs, respectively.

5. The ankle brace of claim 1, wherein the first and second pivot legs comprise multiple extended slots positioned to form a channel for inserting the first and second leg extensions, respectively.

6. The ankle brace of claim 5, wherein each leg extension comprises a securing member sized and shaped to catch between adjacent extended slots such that a user can position the each leg extension at a height desired by the user.

7. The ankle brace of claim 1, wherein the circular openings in each upright leg and the circular pivot openings in each pivot leg have a diameter between 1¼ inches and 2½ inches.

8. The ankle brace of claim 1, further comprising a first and second resilient padding removably attached to an inner surface of each of the first and second pivot legs respectively.

9. The ankle brace of claim 1, further comprising a connectable strap circumscribing at least a portion of the first and second pivot legs, respectively, to tighten the ankle brace about a user's leg.

10. The ankle brace of claim 1, further comprising an orthotic heel correction in a heel portion of the stirrup.

11. The ankle brace of claim 10, wherein the orthotic heel correction comprises a cutaway matched in size and shape with an upraised portion of the heel of the stirrup, the cutaway shaped to prevent rotation of the orthotic heel correction relative to the heel portion of the stirrup.

12. The ankle brace of claim 11, wherein the upraised portion of the heel portion of the stirrup comprises a plurality of arms.

13. The ankle brace of claim 11, wherein the upraised portion of the heel portion of the stirrup comprises three to eight arms.

* * * * *